United States Patent
Ouchi

(10) Patent No.: US 6,921,362 B2
(45) Date of Patent: Jul. 26, 2005

(54) OUTER SHEATHED ENDOSCOPE

(75) Inventor: Teruo Ouchi, Tokyo (JP)

(73) Assignee: PENTAX Corporation, Tokyo (JP)

( * ) Notice: Subject to any disclaimer, the term of this patent is extended or adjusted under 35 U.S.C. 154(b) by 0 days.

(21) Appl. No.: 10/681,155

(22) Filed: Oct. 9, 2003

(65) Prior Publication Data

US 2004/0077927 A1 Apr. 22, 2004

(30) Foreign Application Priority Data

Oct. 10, 2002 (JP) .................................. P. 2002-296913

(51) Int. Cl.⁷ ................................................ A61B 1/00
(52) U.S. Cl. ..................... 600/121; 600/124; 600/125
(58) Field of Search ................................ 600/121–125, 600/127, 129

(56) References Cited

U.S. PATENT DOCUMENTS

| | | | |
|---|---|---|---|
| 5,050,585 A | 9/1991 | Takahashi | |
| 5,125,143 A | 6/1992 | Takahashi | |
| 5,154,164 A | * 10/1992 | Chikama | ..................... 600/124 |
| 5,193,263 A | 3/1993 | Takahashi | |
| 5,257,617 A | 11/1993 | Takahashi | |
| 5,329,935 A | 7/1994 | Takahashi | |
| 5,359,991 A | 11/1994 | Takahashi et al. | |
| 5,662,588 A | * 9/1997 | Iida | ........................... 600/121 |
| 5,674,181 A | * 10/1997 | Iida | ........................... 600/127 |
| 5,685,823 A | 11/1997 | Ito et al. | |
| 5,725,477 A | * 3/1998 | Yasui et al. | ................. 600/127 |
| 5,733,244 A | 3/1998 | Yasui et al. | |
| 5,746,695 A | 5/1998 | Yasui et al. | |
| 5,782,751 A | 7/1998 | Matsuno | |
| 5,788,628 A | 8/1998 | Matsuno et al. | |
| 5,865,726 A | 2/1999 | Katsurada et al. | |
| 5,868,663 A | 2/1999 | Katsurada et al. | |

FOREIGN PATENT DOCUMENTS

| | | |
|---|---|---|
| JP | 3-193023 | 8/1991 |
| JP | 7-33301 | 6/1995 |

* cited by examiner

*Primary Examiner*—Beverly M. Flanagan
(74) *Attorney, Agent, or Firm*—Greenblum & Bernstein, P.L.C.

(57) ABSTRACT

A tip end part (22) of an outer sheath (20) is rotatable about an axis in a predetermined range with respect to a tip end part (13) of a flexible insertion portion (11). A channel deformation space (19) which enables a part in the vicinity of the tip end of a channel tube (23) to be rotated with following the rotation while being elastically deformed is disposed. A locking mechanism (18, 28) is engaged or disengaged by rotating the tip end part (22) of the outer sheath (20) about the axis in the predetermined range with respect to the tip end part (13) of the flexible insertion portion (11).

3 Claims, 6 Drawing Sheets

OUTER SHEATHED ENDOSCOPE

BACKGROUND OF THE INVENTION

The present invention relates to an outer sheathed endoscope having an outer sheath for preventing a flexible insertion portion of the endoscope from being contaminated.

In endoscopy, in order to eliminate infection among patients through an endoscope, a flexible insertion portion of the endoscope is covered by an outer sheath, and the outer sheath is replaced with a new one at each endoscopy.

In order to enable a treatment tool to be used during endoscopy, a channel tube through which the treatment tool is to be passed is formed in the outer sheath, and the channel tube is passed through a guide channel disposed in the flexible insertion portion.

In such an outer sheathed endoscope, during endoscopy, it is required to prevent a tip end part of the outer sheath from being moved with respect to a tip end part of the flexible insertion portion in which an observation window and the like are disposed.

In order to comply with this, conventionally, a locking mechanism is disposed. The locking mechanism is configured by a hook mechanism for restricting the tip end part of the flexible insertion portion from rearward escaping from the tip end of the outer sheath. When the flexible insertion portion is to be pulled out from the outer sheath after endoscopy, a cap-shaped tip end member of the outer sheath is externally pressed to be elastically deformed in a radial direction, thereby disengaging the hook mechanism (for example, Patent literatures Japanese Patent Publication No. H03-193023 and Japanese Utility model Publication No. H07-33301).

When, in order to disengage the hook mechanism, the cap-shaped tip end member of the outer sheath is externally pressed to be elastically deformed, the following cases often arise. The degree of application of the pressing force is not known, and hence the disengagement cannot be well conducted. By contrast, the pressing force is excessively applied, and the tip end member of the outer sheath is broken.

SUMMARY OF THE INVENTION

Therefore, it is an object of the invention to provide an outer sheathed endoscope in which a locking mechanism for restricting a tip end part of a flexible insertion portion from escaping from a tip end part of an outer sheath can be surely engaged and disengaged without producing the possibility of damaging a member.

In order to attain the object, the outer sheathed endoscope of the invention is an outer sheathed endoscope in which a channel tube is passed through an outer sheath for detachably covering a flexible insertion portion of the endoscope, a tip end of the channel tube is fixed to a tip end of the outer sheath, a guide channel through which the channel tube is to be passed in a state where the outer sheath covers the flexible insertion portion is disposed in the flexible insertion portion, and a locking mechanism for restricting a tip end part of the flexible insertion portion from escaping from a tip end part of the outer sheath is disposed, wherein the tip end part of the outer sheath is rotatable about an axis in a predetermined range with respect to the tip end part of the flexible insertion portion, a channel deformation space which enables a part in the vicinity of the tip end of the channel tube to be rotated with following the rotation while being elastically deformed is disposed, and the locking mechanism is engaged or disengaged by rotating the tip end part of the outer sheath about the axis in the predetermined range with respect to the tip end part of the flexible insertion portion.

Alternatively, in a state where the outer sheath covers the flexible insertion portion and no load is applied, a state where the locking mechanism is engaged is maintained by elasticity of the channel tube, and, while elastically deforming the channel tube in the channel deformation space, the tip end part of the outer sheath is rotated about the axis in the predetermined range with respect to the tip end part of the flexible insertion portion, whereby the engagement of the locking mechanism is canceled to enable the tip end part of the flexible insertion portion to escape from the tip end part of the outer sheath.

Alternatively, the locking mechanism has: an L-shaped groove portion which is formed in an outer face of the tip end part of the flexible insertion portion; and a hook portion which is formed on an inner face of the tip end part of the outer sheath to be engageable and disengageable with the groove portion.

DETAILED DESCRIPTION OF PREFERRED EMBODIMENTS

An embodiment of the invention will be described with reference to the accompanying drawings.

Figure 2:
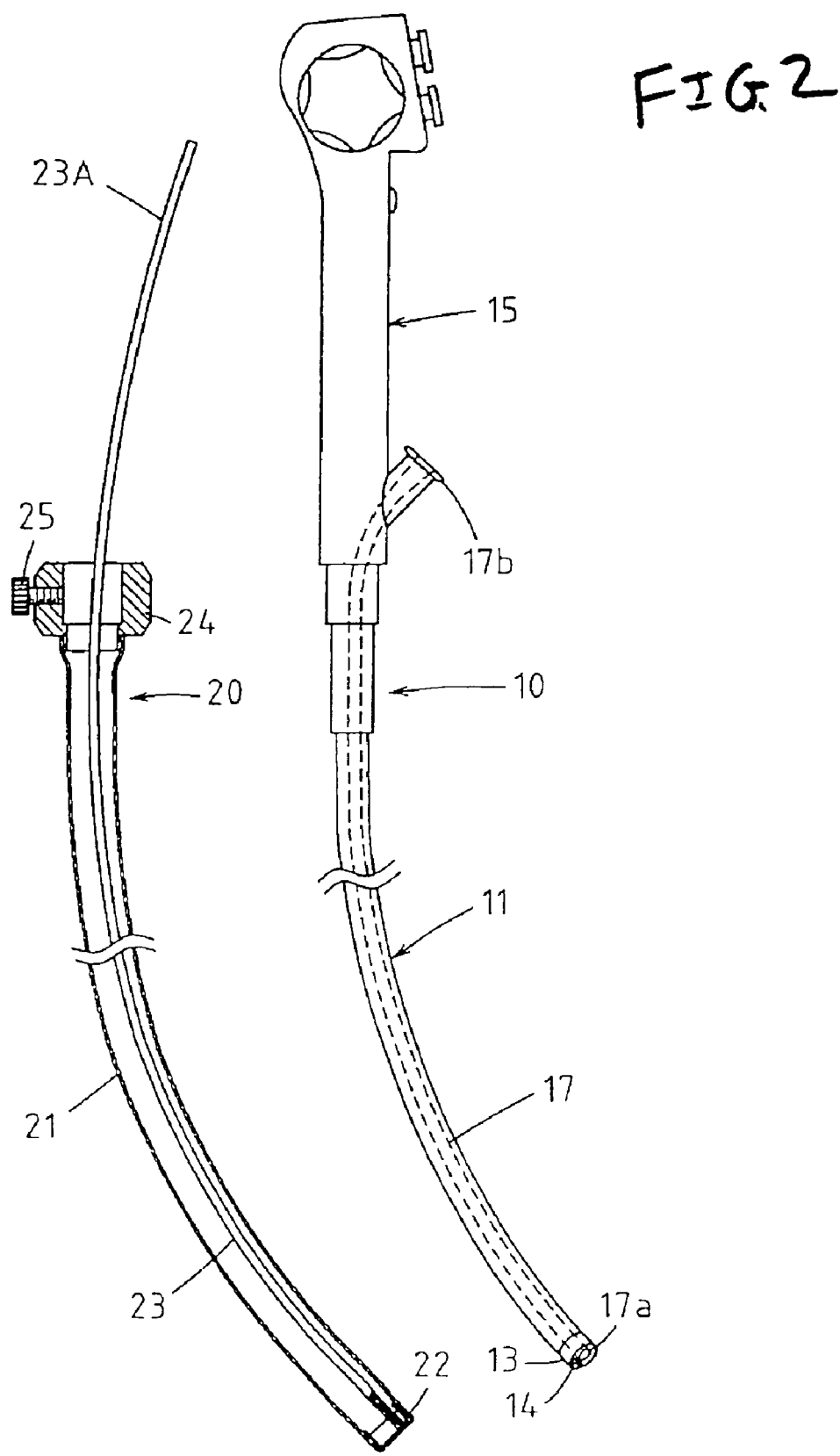
FIG. 2 is a side view showing the state where the outer sheath is detached from the flexible insertion portion of the outer sheathed endoscope of the embodiment of the invention, partly in section.

FIG. 2 shows an example of an endoscope 10, and an outer sheath 20 which is to detachably cover a flexible insertion portion 11 of the endoscope 10. In the figure, a sectional shape of the outer sheath 20 is shown, and the external shape of the endoscope 10 is shown.

A tip end body 13 in which an observation window 14 and the like are placed is coupled to the tip end of the flexible insertion portion 11 of the endoscope 10. The basal end of the flexible insertion portion 11 is coupled to the lower end of an operation portion 15.

A guide channel 17 which is formed by, for example, a flexible polyethylene resin tube is passed through the whole length of the flexible insertion portion 11. A tip end opening 17a of the channel is formed at a position which is deviated from the center of the end face of the tip end body 13. The basal end of the guide channel 17 communicates with a basal end opening 17b which is protrudingly formed on the operation portion 15.

During endoscopy, the outer sheath 20 covers the flexible insertion portion 11 in order to prevent the endoscope 10 from being contaminated by the body fluid or the like of the subject. A cover tube 21 which is formed into a thin cylindrical shape by an elastic material, such as a silicone rubber tube is disposed so as to detachably cover the flexible insertion portion 11 of the endoscope 10.

An end cap 22 which is formed by a transparent member, and which is to be fitted onto the tip end body 13 of the endoscope 10 is watertightly attached to the tip end of the cover tube 21.

A coupling ring 24 which is fixed to the basal end of the cover tube 21 is engageable and disengageable with a coupling portion between the flexible insertion portion 11 of the endoscope 10 and the operation portion 15, and can be arbitrarily fixed to the coupling portion by fastening a manual fixing screw 25.

A channel tube 23 which is formed by a slippery material, such as a flexible tetrafluoroethylene resin tube is passed through the whole length of the cover tube 21 in the axial direction.

The tip end of the channel tube 23 is fixed to the end cap 22 so as to be opened to the outer face in the end face of the end cap 22. A basal end part 23A of the channel tube 23 elongates rearward with passing through the coupling ring 24.

The channel tube 23 is insertable and extractable over the whole length of the guide channel 17 of the endoscope 10. The basal end part 23A of the channel tube 23 can be inserted into the tip end opening 17a of the guide channel 17 and then pulled out from the basal end opening 17b in the opposite end.

Figure 1:
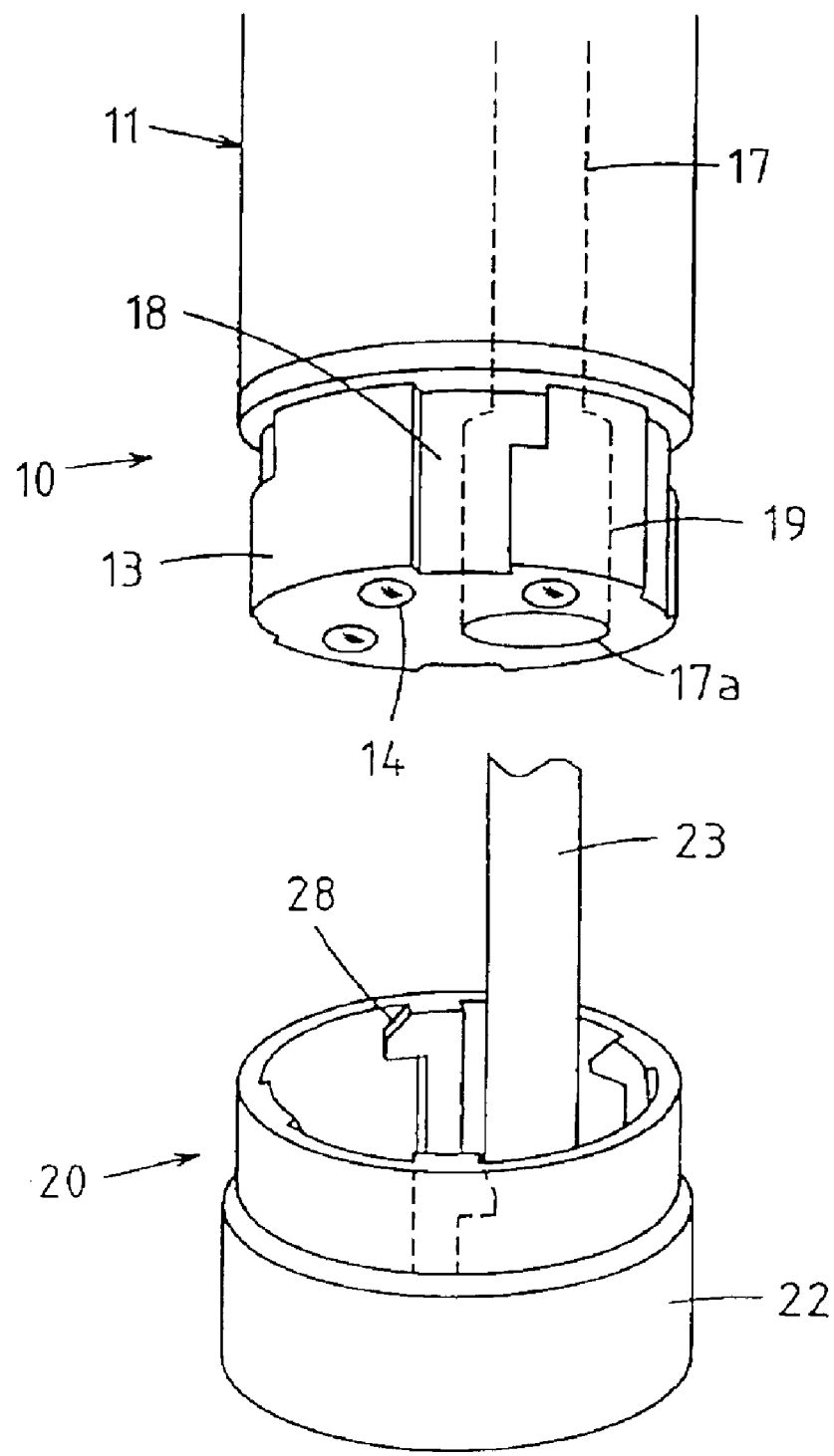
FIG. 1 is a partial perspective view showing a state where an outer sheath is detached from a flexible insertion portion of an outer sheathed endoscope of an embodiment of the invention.
Figure 3:
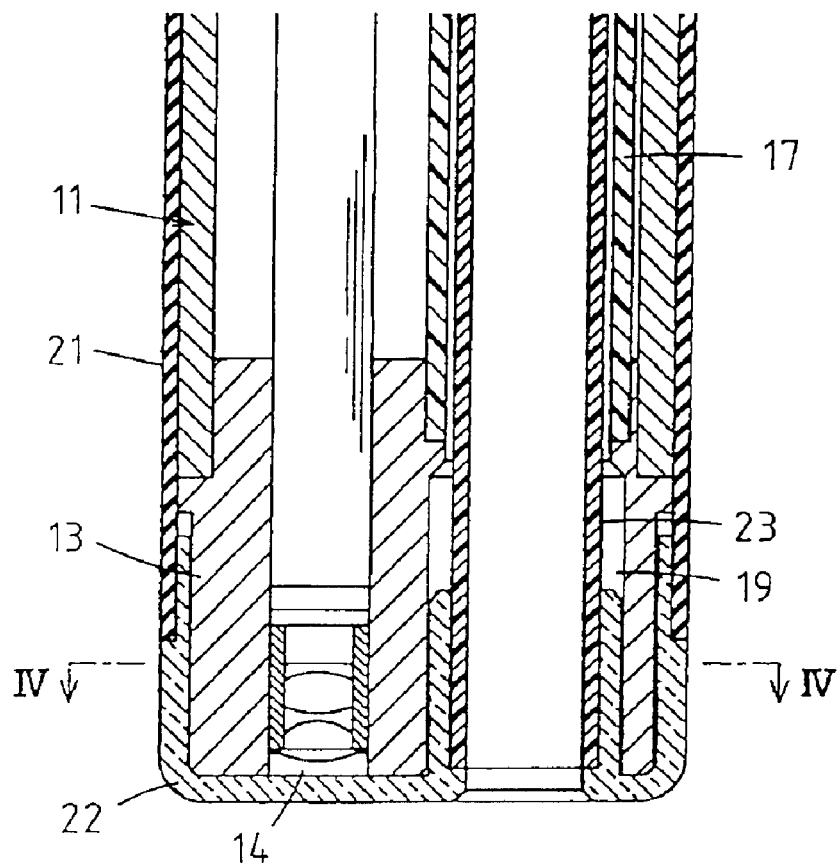
FIG. 3 is a side section view showing a tip end part in a state where the outer sheath covers the flexible insertion portion of the outer sheathed endoscope of the embodiment of the invention.

FIG. 3 shows the tip end part in a state where the flexible insertion portion 11 of the endoscope 10 is covered by the outer sheath 20, and FIG. 1 shows a state where the end cap 22 is detached from the tip end body 13, with omitting the cover tube 21.

As shown in FIG. 3, in the state where the flexible insertion portion 11 is covered by the outer sheath 20, the inner end face of the end cap 22 is in close contact with the outer end face of the tip end body 13, and the channel tube 23 of the outer sheath 20 is passed through the guide channel 17 of the endoscope 10.

Although the end cap 22 is fitted onto the tip end body 13 so as to be rotatable about the axis, the rotation is restricted by the insertion of the channel tube 23 into the guide channel 17.

Figure 4:
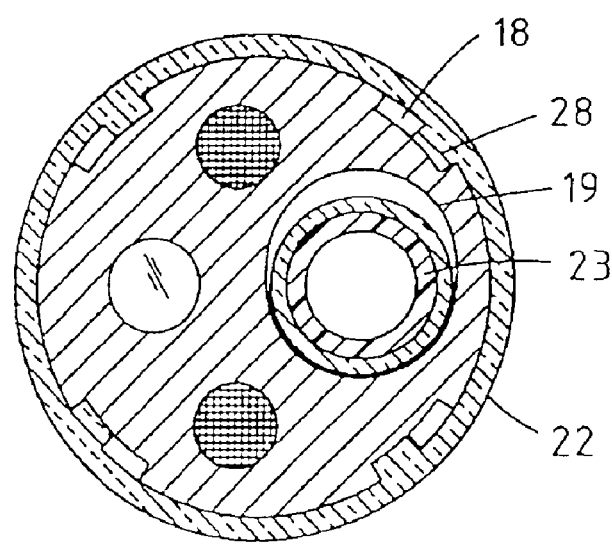
FIG. 4 is a section view of the embodiment of the invention taken along line IV—IV in FIG. 3.

As indicated in FIG. 4 showing a section along line IV-IV, however, a channel deformation space 19 in which a part in the vicinity of the tip end of the channel tube 23 can be rotated about the axis of the end cap 22 while being deformed (this is substantially elastic deformation) is formed in a portion of the tip end body 13 through which the channel tube 23 is to be passed. The end cap 22 can be rotated about the tip end body 13 in a range of the elastic deformation of the channel tube 23 in the channel deformation space 19.

As shown in the figures such as FIG. 1, a locking mechanism configured by hook portions 28 and groove portions 18, and for restricting the tip end body 13 from rearward escaping from the end cap 22 is disposed in the end cap 22 and the tip end body 13.

In the embodiment, the hook portions 28 are formed with protruding in an L-like shape respectively from four places of the inner peripheral face of the end cap 22, and the groove portions 18 are formed with being recessed in an L-like shape respectively in four places of the outer peripheral face of the tip end body 13 so that the corresponding hook portions 28 can be engaged with and disengaged from the groove portions.

Figure 5:
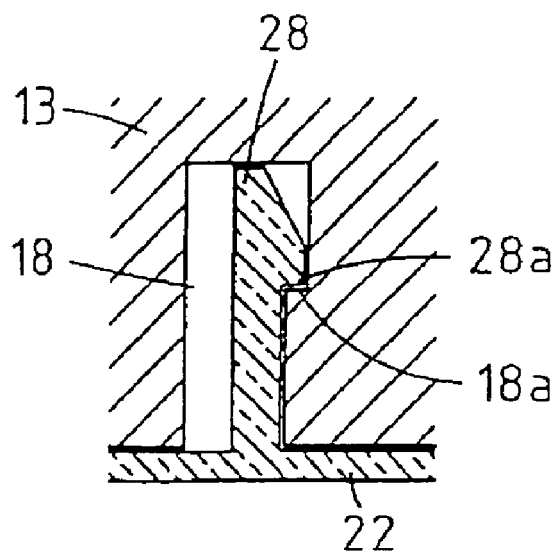
FIG. 5 is a side section view of an engaged state of a locking mechanism in the embodiment of the invention.

FIG. 5 shows an engagement state of one of the hook portions 28 and the corresponding one of the groove portions 18. A hook part 28a of the hook portion 28 is engaged with a step part 18a of the groove portion 18 to form a locked state where the end cap 22 and the tip end body 13 cannot be relatively moved in the axial direction.

As shown in the figures such as FIG. 4, however, the groove portions 18 are formed so as to be wider than the hook portions 28 in the circumferential direction. When the end cap 22 is rotated about the tip end body 13, therefore, the hook part 28a of each hook portion 28 is disengaged from the step part 18a of the groove portion 18 as shown in FIG. 6, thereby forming a lock canceling state where the tip end body 13 can be rearward pulled out from the end cap 22.

Figure 7:
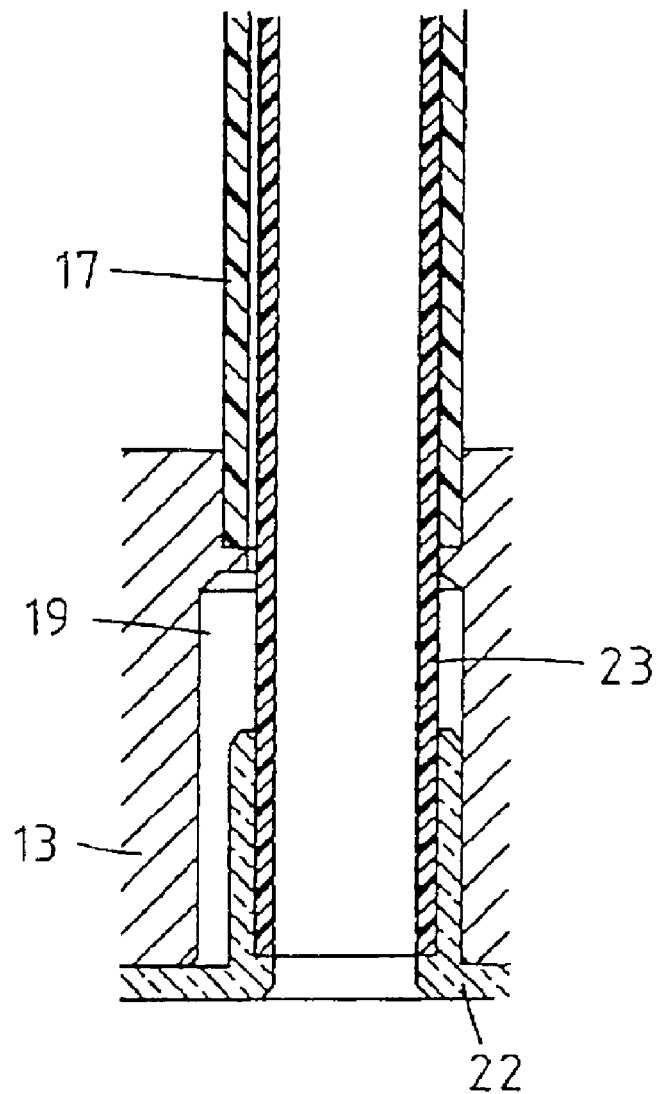
FIG. 7 is a side section view showing a state of a channel tube in a channel deformation space in a usual state of the embodiment of the invention.

In the thus configured embodiment, in a usual state where the outer sheath 20 covers the flexible insertion portion 11 and no special load is applied to the end cap 22, the channel tube 23 in the channel deformation space 19 is made straight by its elasticity so as to be substantially parallel to the axis of the end cap 22 as shown in FIG. 7, and the locking state where the hook portions 28 are engaged with the groove portions 18 as shown in FIG. 5 is maintained.

Figure 6:
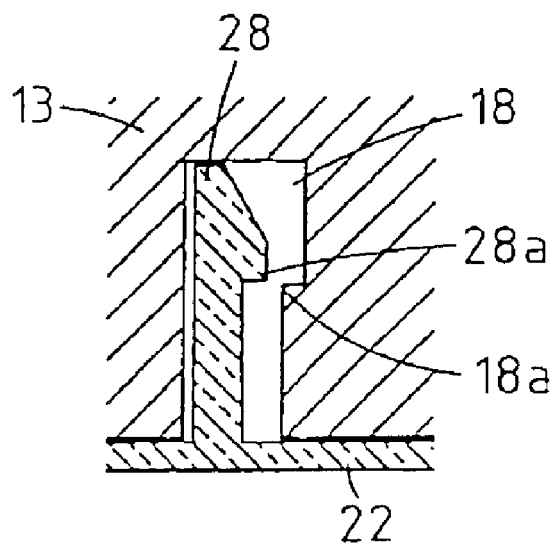
FIG. 6 is a side section view of a disengaged state of the locking mechanism in the embodiment of the invention.
Figure 8:
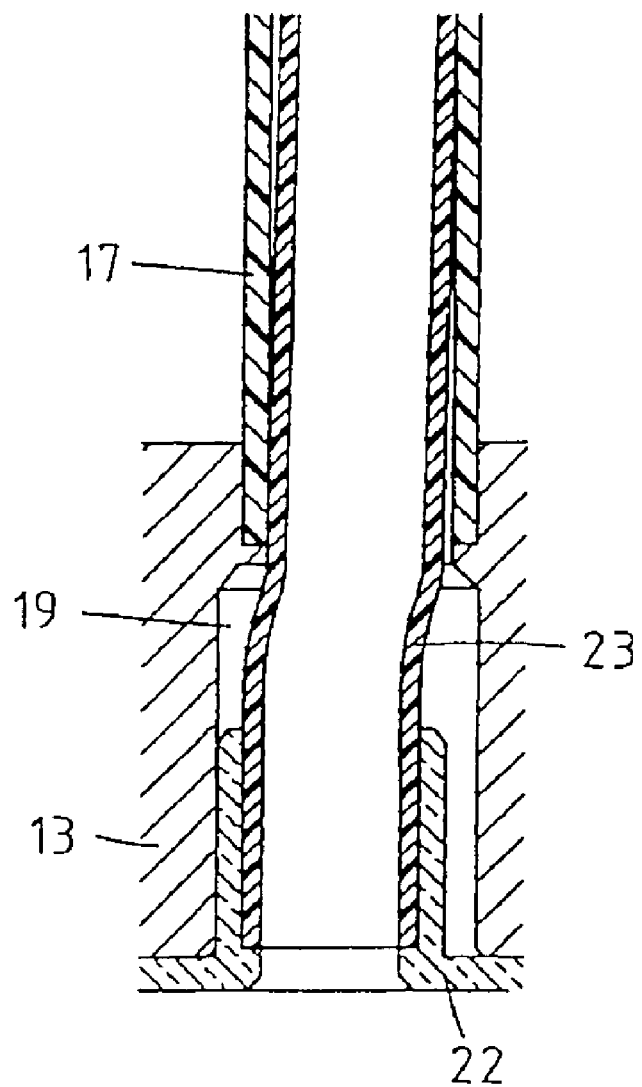
FIG. 8 is a side section view showing a state of the channel tube in the channel deformation space when the locking mechanism in the embodiment of the invention is engaged or disengaged.

When the end cap 22 in this state is rotated about the tip end body 13, the channel tube 23 is rotated with following the rotation while being elastically deformed in the channel deformation space 19 as shown in FIG. 8, thereby producing the lock canceling state where the engagement between the hook portions 28 and the groove portions 18 is cancelled as shown in FIG. 6. As a result, the flexible insertion portion 11 can be rearward pulled out from the outer sheath 20.

When the outer sheath 20 is to cover the flexible insertion portion 11, the hook portions 28 can be smoothly inserted into the groove portions 18 because an edge of the tip end of each hook portion 28 is formed as an inclined face.

In this case, the channel tube 23 in the channel deformation space 19 is in the elastically deformed state shown in FIG. 8. After the engagement between the hook portions 28 and the groove portions 18 is established, the channel tube 23 is returned by its elasticity to the usual or straight state shown in FIG. 7, thereby forming the locking state shown in FIG. 5.

The invention is not restricted to the embodiment. For example, the invention can be applied in the same manner as the embodiment, on a configuration in which the guide channel 17 is not passed through the flexible insertion portion 11, but formed as a channel that is formed by recessing the outer face of the flexible insertion portion 11.

According to the invention, engagement and disengagement of the locking mechanism for restricting the tip end part of the flexible insertion portion from escaping from the tip end part of the outer sheath are performed by rotating the tip end part of the outer sheath about the axis with respect to the tip end part of the flexible insertion portion in the range where the channel tube is elastically deformed in the channel deformation space. Therefore, the locking mechanism can be surely engaged and disengaged without producing the possibility of damaging a member.

What is claimed is:

1. An outer sheathed endoscope comprising:

a flexible insertion portion having a guide channel formed therethrough;

a detachable outer sheath covering the flexible insertion portion;

a channel tube, a tip end of the channel tube being fixed to a tip end of the outer sheath and passing through the outer sheath, wherein when the outer sheath covers the flexible insertion portion, the channel tube extends through the guide channel;

a locking mechanism for restricting the flexible insertion portion from detaching from the outer sheath; and a channel deformation space that permits a part in the vicinity of a tip end part of the channel tube to be elastically deformed when a tip end part of the outer sheath is rotated about an axis in a predetermined range in a circumferential direction with respect to the tip end part of the flexible insertion portion, wherein the locking mechanism is disengaged by rotating the tip end part of the outer sheath about the axis in the predetermined range with respect to the tip end part of the flexible insertion portions, wherein the locking mechanism includes a hook portion and a groove portion, the groove portion being engageable with the hook portion in the circumferential direction, and wherein the hook portion is disengaged from the groove portion when the tip end part of the outer sheath is rotated with respect to the tip end cart of the flexible insertion portion.

2. The outer sheathed endoscope according to claim 1, wherein when the outer sheath covers the flexible insertion portion and no load is applied to the outer sheath, the locking mechanism is engaged by elasticity of the channel tube, and the engagement of the locking mechanism is removed to enable the tip end part of the flexible insertion portion to detach from the tip end part of the outer sheath when the tip end part of the outer sheath is rotated about the axis in the predetermined range with respect to the tip end part of the flexible insertion portion by elastically deforming the channel tube in the channel deformation space.

3. The outer sheathed endoscope according to claim 1, wherein the locking mechanism includes an L-shaped groove portion that is provided in an outer face of the tip end part of the flexible insertion portion and a hook portion that is provided on an inner face of the tip end part of the outer sheath to be engageable with the groove portion.

* * * * *